(12) United States Patent
Hinchliffe

(10) Patent No.: US 7,909,801 B2
(45) Date of Patent: Mar. 22, 2011

(54) DOUBLE BALLOON THROMBECTOMY CATHETER

(75) Inventor: Peter W. J. Hinchliffe, Campbell Hall, NY (US)

(73) Assignee: Rex Medical, L.P., Conshohocken, PA (US)

( * ) Notice: Subject to any disclaimer, the term of this patent is extended or adjusted under 35 U.S.C. 154(b) by 0 days.

(21) Appl. No.: 12/631,787

(22) Filed: Dec. 4, 2009

(65) Prior Publication Data

US 2010/0082052 A1    Apr. 1, 2010

Related U.S. Application Data

(63) Continuation of application No. 11/267,379, filed on Nov. 4, 2005, now Pat. No. 7,645,261, which is a continuation of application No. 09/888,149, filed on Jun. 22, 2001, now abandoned, which is a continuation-in-part of application No. PCT/US00/41355, filed on Oct. 20, 2000.

(60) Provisional application No. 60/214,331, filed on Jun. 27, 2000, provisional application No. 60/161,124, filed on Oct. 22, 1999.

(51) Int. Cl.
    *A61M 5/00* (2006.01)

(52) U.S. Cl. ...................................................... 604/247

(58) Field of Classification Search ............... 604/96.01, 604/101.01; 606/191–194
See application file for complete search history.

(56) References Cited

U.S. PATENT DOCUMENTS

| | | |
|---|---|---|
| 2,756,752 A | 7/1956 | Scherlis |
| 3,108,594 A | 10/1963 | Glassman |
| 3,612,058 A | 10/1971 | Ackerman |
| 3,741,214 A | 6/1973 | Tillander |
| 3,749,085 A | 7/1973 | Willson et al. |
| 3,841,308 A | 10/1974 | Tate |
| 4,030,503 A | 6/1977 | Clark, III |
| 4,276,874 A | 7/1981 | Wolvek et al. |
| 4,559,046 A | 12/1985 | Groshong et al. |
| 4,579,127 A | 4/1986 | Haacke |
| 4,614,188 A | 9/1986 | Bazell et al. |
| 4,646,736 A | 3/1987 | Auth |
| 4,664,112 A | 5/1987 | Kensey et al. |
| 4,676,778 A | 6/1987 | Nelson, Jr. |
| 4,706,671 A | 11/1987 | Weinrib |
| 4,732,154 A | 3/1988 | Shiber |
| 4,745,919 A | 5/1988 | Bundy et al. |
| 4,794,928 A | 1/1989 | Kletschka |
| 4,819,634 A | 4/1989 | Shiber |

(Continued)

FOREIGN PATENT DOCUMENTS

DE       3640034        5/1988

(Continued)

OTHER PUBLICATIONS

Rex Medical website—www.rexmedical.com—home page (Jul. 2000).

(Continued)

*Primary Examiner* — Manuel A Mendez
(74) *Attorney, Agent, or Firm* — Neil D. Gershon

(57) ABSTRACT

A catheter has a lumen for a thrombectomy device and at least two balloons of different compliancies. In one embodiment, the catheter is adapted to clear dialysis grafts. One balloon is adapted to expand a stenosis at a venous junction of a dialysis graft and another balloon is adapted to pull a stenosis at an arterial junction of a dialysis graft. A single catheter may be used to perform a dialysis thrombectomy procedure.

17 Claims, 4 Drawing Sheets

U.S. PATENT DOCUMENTS

| | | |
|---|---|---|
| 4,883,460 A | 11/1989 | Zanetti |
| 4,935,025 A | 6/1990 | Bundy et al. |
| 4,984,581 A | 1/1991 | Stice |
| 4,986,807 A | 1/1991 | Farr |
| 4,994,067 A | 2/1991 | Summers |
| 5,002,553 A | 3/1991 | Shiber |
| RE33,569 E | 4/1991 | Gifford et al. |
| 5,007,896 A | 4/1991 | Shiber |
| 5,009,659 A | 4/1991 | Hamlin et al. |
| 5,011,488 A | 4/1991 | Ginsburg |
| 5,011,489 A | 4/1991 | Salem |
| 5,011,490 A | 4/1991 | Fischell et al. |
| 5,019,088 A | 5/1991 | Farr |
| 5,019,089 A | 5/1991 | Farr |
| 5,024,651 A | 6/1991 | Shiber |
| 5,026,383 A | 6/1991 | Nobles |
| 5,026,384 A | 6/1991 | Farr et al. |
| 5,041,217 A | 8/1991 | Reid |
| 5,042,984 A | 8/1991 | Kensey et al. |
| 5,047,040 A | 9/1991 | Simpson et al. |
| 5,047,041 A | 9/1991 | Samuels |
| 5,049,124 A | 9/1991 | Bales |
| 5,049,154 A | 9/1991 | Quadri |
| 5,053,044 A | 10/1991 | Mueller et al. |
| 5,054,501 A | 10/1991 | Chuttani et al. |
| 5,059,203 A | 10/1991 | Husted |
| 5,061,240 A | 10/1991 | Cherian |
| 5,062,648 A | 11/1991 | Gomringer |
| 5,069,662 A | 12/1991 | Bodden |
| 5,069,679 A | 12/1991 | Taheri |
| 5,071,424 A | 12/1991 | Reger |
| 5,071,425 A | 12/1991 | Gifford et al. |
| 5,074,841 A | 12/1991 | Ademovic et al. |
| 5,078,722 A | 1/1992 | Stevens |
| 5,078,723 A | 1/1992 | Dance et al. |
| 5,084,010 A | 1/1992 | Plaia et al. |
| 5,085,662 A | 2/1992 | Willard |
| 5,087,264 A | 2/1992 | Miller et al. |
| 5,087,265 A | 2/1992 | Summers |
| 5,092,839 A | 3/1992 | Kipperman |
| 5,092,872 A | 3/1992 | Segalowitz |
| 5,092,873 A | 3/1992 | Simpson et al. |
| 5,097,849 A | 3/1992 | Kensey et al. |
| 5,100,423 A | 3/1992 | Fearnot |
| 5,100,424 A | 3/1992 | Jang et al. |
| 5,100,425 A | 3/1992 | Fischell et al. |
| 5,100,426 A | 3/1992 | Nixon |
| 5,102,415 A | 4/1992 | Guenther |
| 5,108,411 A | 4/1992 | McKenzie |
| 5,108,419 A | 4/1992 | Reger et al. |
| 5,112,347 A | 5/1992 | Taheri |
| 5,114,399 A | 5/1992 | Kovalcheck |
| 5,116,350 A | 5/1992 | Stevens |
| 5,116,352 A | 5/1992 | Schnepp-Pesch et al. |
| 5,127,902 A | 7/1992 | Fischell |
| 5,127,917 A | 7/1992 | Niederhauser et al. |
| 5,131,379 A | 7/1992 | Sewell |
| 5,133,725 A | 7/1992 | Quadri |
| 5,135,482 A | 8/1992 | Neracher |
| 5,135,484 A | 8/1992 | Wright |
| 5,135,531 A | 8/1992 | Shiber |
| 5,139,506 A | 8/1992 | Bush |
| 5,141,491 A | 8/1992 | Bowald |
| 5,141,503 A | 8/1992 | Sewell |
| 5,152,771 A | 10/1992 | Sabbaghian et al. |
| 5,152,772 A | 10/1992 | Sewell |
| 5,152,773 A | 10/1992 | Redha |
| 5,154,724 A | 10/1992 | Andrews |
| 5,156,610 A | 10/1992 | Reger |
| 5,158,564 A | 10/1992 | Schnepp-Pesch et al. |
| 5,160,342 A | 11/1992 | Reger et al. |
| 5,163,421 A | 11/1992 | Bernstein et al. |
| 5,170,805 A | 12/1992 | Kensey et al. |
| 5,171,316 A | 12/1992 | Mehigan |
| 5,176,693 A | 1/1993 | Pannek |
| 5,178,625 A | 1/1993 | Groshong |
| 5,181,920 A | 1/1993 | Mueller et al. |
| 5,192,268 A | 3/1993 | Shiber |
| 5,192,290 A | 3/1993 | Hilal |
| 5,192,291 A | 3/1993 | Pannek |
| 5,195,954 A | 3/1993 | Schnepp-Pesch et al. |
| 5,195,956 A | 3/1993 | Stockmeier |
| 5,196,024 A | 3/1993 | Barath |
| 5,197,485 A | 3/1993 | Grooters |
| 5,201,750 A | 4/1993 | Hecherl et al. |
| 5,209,749 A | 5/1993 | Buelna |
| 5,211,651 A | 5/1993 | Reger et al. |
| 5,211,683 A | 5/1993 | Maginot |
| 5,217,026 A | 6/1993 | Stoy et al. |
| 5,217,453 A | 6/1993 | Wilk |
| 5,217,474 A | 6/1993 | Zacca et al. |
| 5,222,965 A | 6/1993 | Haughton |
| 5,222,966 A | 6/1993 | Perkins et al. |
| 5,224,945 A | 7/1993 | Pannek |
| 5,224,949 A | 7/1993 | Gomringer et al. |
| 5,226,909 A | 7/1993 | Evans et al. |
| 5,234,450 A | 8/1993 | Segalowitz |
| 5,234,451 A | 8/1993 | Osypka |
| 5,242,460 A | 9/1993 | Klein et al. |
| 5,242,461 A | 9/1993 | Kortenback et al. |
| 5,248,296 A | 9/1993 | Alliger |
| 5,250,059 A | 10/1993 | Andreas et al. |
| 5,250,060 A | 10/1993 | Carbo et al. |
| 5,251,640 A | 10/1993 | Osborne |
| 5,261,877 A | 11/1993 | Fine et al. |
| 5,262,593 A | 11/1993 | Madry et al. |
| 5,267,954 A | 12/1993 | Nita |
| 5,269,751 A | 12/1993 | Kaliman et al. |
| 5,269,793 A | 12/1993 | Simpson |
| 5,282,484 A | 2/1994 | Reger |
| 5,282,813 A | 2/1994 | Redha |
| 5,284,478 A | 2/1994 | Nobles et al. |
| 5,284,486 A | 2/1994 | Kotula et al. |
| 5,295,958 A | 3/1994 | Shturman |
| 5,300,025 A | 4/1994 | Wantink |
| 5,303,719 A | 4/1994 | Wilk et al. |
| 5,304,189 A | 4/1994 | Goldberg et al. |
| 5,304,220 A | 4/1994 | Maginot |
| 5,306,244 A | 4/1994 | Shiber |
| 5,308,354 A | 5/1994 | Zacca et al. |
| 5,312,425 A | 5/1994 | Evans et al. |
| 5,312,427 A | 5/1994 | Shturman |
| 5,313,967 A | 5/1994 | Lieber et al. |
| 5,314,407 A | 5/1994 | Auth et al. |
| 5,314,438 A | 5/1994 | Shturman |
| 5,318,576 A | 6/1994 | Plassche et al. |
| 5,320,599 A | 6/1994 | Griep et al. |
| 5,320,634 A | 6/1994 | Vigil et al. |
| 5,334,211 A | 8/1994 | Shiber |
| 5,336,167 A | 8/1994 | Sullivan et al. |
| 5,336,234 A | 8/1994 | Vigil et al. |
| 5,342,394 A | 8/1994 | Matsuno et al. |
| 5,344,395 A | 9/1994 | Whalen et al. |
| 5,345,940 A | 9/1994 | Seward et al. |
| 5,345,945 A | 9/1994 | Hodgson et al. |
| 5,346,473 A | 9/1994 | Bowman |
| 5,348,017 A | 9/1994 | Thornton et al. |
| 5,350,390 A | 9/1994 | Sher |
| 5,352,232 A | 10/1994 | Cohen |
| 5,356,418 A | 10/1994 | Shturman |
| 5,358,472 A | 10/1994 | Vance et al. |
| 5,358,485 A | 10/1994 | Vance et al. |
| 5,358,507 A | 10/1994 | Daily |
| 5,358,509 A | 10/1994 | Fine et al. |
| 5,360,432 A | 11/1994 | Shturman |
| 5,360,433 A | 11/1994 | Medl |
| 5,366,463 A | 11/1994 | Ryan |
| 5,366,464 A | 11/1994 | Belknap |
| 5,368,603 A | 11/1994 | Halliburton |
| 5,370,609 A | 12/1994 | Drasler et al. |
| 5,370,651 A | 12/1994 | Summers |
| 5,370,653 A | 12/1994 | Cragg |
| 5,372,144 A | 12/1994 | Mortier et al. |
| 5,372,601 A | 12/1994 | Lary |
| 5,376,100 A | 12/1994 | Lefebvre et al. |
| 5,383,460 A | 1/1995 | Jang et al. |
| 5,395,311 A | 3/1995 | Andrews |

| Patent No. | Date | Inventor |
|---|---|---|
| 5,395,315 A | 3/1995 | Griep |
| 5,395,384 A | 3/1995 | Duthoit |
| 5,402,790 A | 4/1995 | Jang et al. |
| 5,403,334 A | 4/1995 | Evans et al. |
| 5,409,454 A | 4/1995 | Fischell et al. |
| 5,411,509 A | 5/1995 | Hilal |
| 5,417,703 A | 5/1995 | Brown et al. |
| 5,419,774 A | 5/1995 | Willard et al. |
| 5,423,799 A | 6/1995 | Shiu |
| 5,423,838 A | 6/1995 | Willard |
| 5,429,136 A | 7/1995 | Milo et al. |
| 5,441,510 A | 8/1995 | Simpson et al. |
| 5,449,369 A | 9/1995 | Imran |
| 5,449,372 A | 9/1995 | Schmaltz et al. |
| 5,451,208 A | 9/1995 | Goldrath |
| 5,453,088 A | 9/1995 | Boudewijn et al. |
| 5,462,529 A | 10/1995 | Simpson et al. |
| 5,476,450 A | 12/1995 | Ruggio |
| 5,480,379 A | 1/1996 | La Rosa |
| 5,484,412 A | 1/1996 | Pierpont |
| 5,488,958 A | 2/1996 | Topel et al. |
| 5,490,859 A | 2/1996 | Mische et al. |
| 5,496,267 A | 3/1996 | Drasler et al. |
| 5,497,782 A | 3/1996 | Fugoso |
| 5,501,694 A | 3/1996 | Ressemann et al. |
| 5,507,292 A | 4/1996 | Jang et al. |
| 5,507,760 A | 4/1996 | Wynne et al. |
| 5,507,761 A | 4/1996 | Duer |
| 5,512,044 A | 4/1996 | Duer |
| 5,514,092 A | 5/1996 | Forman et al. |
| 5,514,115 A | 5/1996 | Frantzen et al. |
| 5,514,150 A | 5/1996 | Rostoker |
| 5,514,151 A | 5/1996 | Fogarty et al. |
| 5,520,635 A | 5/1996 | Gelbfish |
| 5,522,824 A | 6/1996 | Ashby |
| 5,522,825 A | 6/1996 | Kropf et al. |
| 5,522,826 A | 6/1996 | Daily |
| 5,527,325 A | 6/1996 | Conley et al. |
| 5,527,326 A | 6/1996 | Hermann et al. |
| 5,527,327 A | 6/1996 | Louw et al. |
| 5,527,330 A | 6/1996 | Tovey |
| 5,536,242 A | 7/1996 | Willard et al. |
| 5,540,656 A | 7/1996 | Pflueger et al. |
| 5,540,707 A | 7/1996 | Ressemann et al. |
| 5,542,917 A | 8/1996 | Nita et al. |
| 5,542,925 A | 8/1996 | Orth |
| 5,547,469 A | 8/1996 | Rowland et al. |
| 5,551,443 A | 9/1996 | Sepetka et al. |
| 5,554,163 A | 9/1996 | Shturman |
| 5,556,405 A | 9/1996 | Lary |
| 5,556,408 A | 9/1996 | Farhat |
| 5,562,275 A | 10/1996 | Weissenfluh et al. |
| 5,562,701 A | 10/1996 | Huiteme et al. |
| 5,569,204 A | 10/1996 | Cramer |
| 5,569,275 A | 10/1996 | Kotula et al. |
| 5,569,276 A | 10/1996 | Jang et al. |
| 5,569,277 A | 10/1996 | Evans et al. |
| 5,569,279 A | 10/1996 | Rainin |
| 5,571,122 A | 11/1996 | Kelly et al. |
| 5,571,130 A | 11/1996 | Simpson et al. |
| 5,571,167 A | 11/1996 | Maginot |
| 5,584,842 A | 12/1996 | Fogarty et al. |
| 5,584,843 A | 12/1996 | Wulfman et al. |
| 5,591,183 A | 1/1997 | Chin |
| 5,591,184 A | 1/1997 | McDonnell et al. |
| 5,599,307 A | 2/1997 | Bacher et al. |
| 5,601,580 A | 2/1997 | Goldberg et al. |
| 5,601,581 A | 2/1997 | Fogarty et al. |
| 5,605,162 A | 2/1997 | Mirzaee et al. |
| 5,609,602 A | 3/1997 | Machemer et al. |
| 5,616,149 A | 4/1997 | Barath |
| 5,622,188 A | 4/1997 | Plaia et al. |
| 5,624,455 A | 4/1997 | Matsuno |
| 5,624,457 A | 4/1997 | Farley et al. |
| 5,626,562 A | 5/1997 | Castro |
| 5,626,593 A | 5/1997 | Imran |
| 5,626,597 A | 5/1997 | Urban et al. |
| 5,628,746 A | 5/1997 | Clayman |
| 5,628,761 A | 5/1997 | Rizik |
| 5,630,823 A | 5/1997 | Schmitz-Rode et al. |
| 5,632,755 A | 5/1997 | Nordgren et al. |
| 5,643,199 A | 7/1997 | Rowland et al. |
| 5,643,296 A | 7/1997 | Hundertmark et al. |
| 5,643,297 A | 7/1997 | Nordgren et al. |
| 5,643,298 A | 7/1997 | Nordgren et al. |
| 5,649,941 A | 7/1997 | Lary |
| 5,649,946 A | 7/1997 | Bramlet |
| 5,653,722 A | 8/1997 | Kieturakis |
| 5,658,282 A | 8/1997 | Daw et al. |
| 5,658,301 A | 8/1997 | Lemaitre et al. |
| 5,658,302 A | 8/1997 | Wicherski et al. |
| 5,662,603 A | 9/1997 | Gelbfish |
| 5,662,671 A | 9/1997 | Barbut et al. |
| 5,662,701 A | 9/1997 | Plaia et al. |
| 5,665,093 A | 9/1997 | Atkins |
| 5,665,098 A | 9/1997 | Kelly et al. |
| 5,667,480 A | 9/1997 | Knight et al. |
| 5,669,920 A | 9/1997 | Conley |
| 5,674,226 A | 10/1997 | Doherty et al. |
| 5,674,232 A | 10/1997 | Halliburton |
| 5,681,335 A | 10/1997 | Serra et al. |
| 5,681,336 A | 10/1997 | Clement et al. |
| 5,683,362 A | 11/1997 | Rowland et al. |
| 5,688,234 A | 11/1997 | Frisbie |
| 5,695,506 A | 12/1997 | Pike et al. |
| 5,695,507 A | 12/1997 | Auth et al. |
| 5,695,508 A | 12/1997 | Chigogidze |
| 5,695,514 A | 12/1997 | Chin |
| 5,697,944 A | 12/1997 | Lary |
| 5,700,240 A | 12/1997 | Barwick et al. |
| 5,702,412 A | 12/1997 | Popov et al. |
| 5,702,413 A | 12/1997 | Lafontaine |
| 5,728,123 A | 3/1998 | Lemelson et al. |
| 5,733,296 A | 3/1998 | Rogers et al. |
| 5,746,758 A | 5/1998 | Nordgren et al. |
| 5,755,968 A | 5/1998 | Stone |
| 5,766,191 A | 6/1998 | Trerotola |
| 5,766,192 A | 6/1998 | Zacca |
| 5,776,153 A | 7/1998 | Rees |
| 5,830,156 A | 11/1998 | Ali |
| 5,833,631 A | 11/1998 | Nguyen |
| 5,833,644 A | 11/1998 | Zadno-Azizi et al. |
| 5,840,046 A | 11/1998 | Deem |
| 5,843,103 A | 12/1998 | Wulfman |
| 5,876,413 A | 3/1999 | Fogarty et al. |
| 5,876,414 A | 3/1999 | Straub |
| 5,882,329 A | 3/1999 | Patterson et al. |
| 5,885,227 A | 3/1999 | Finlayson |
| 5,895,398 A | 4/1999 | Wensel et al. |
| 5,902,263 A | 5/1999 | Patterson et al. |
| 5,904,679 A | 5/1999 | Clayman |
| 5,910,364 A | 6/1999 | Miyata et al. |
| 5,916,166 A | 6/1999 | Reiss et al. |
| 5,919,163 A | 7/1999 | Glickman |
| 5,938,623 A | 8/1999 | Quiachon et al. |
| 5,941,869 A | 8/1999 | Patterson et al. |
| 5,947,985 A | 9/1999 | Imran |
| 5,954,737 A | 9/1999 | Lee |
| 5,971,991 A | 10/1999 | Sunderland |
| 5,972,019 A | 10/1999 | Engelson et al. |
| 5,984,877 A | 11/1999 | Fleischhacker, Jr. |
| 6,001,068 A | 12/1999 | Uchino et al. |
| 6,001,112 A | 12/1999 | Taylor |
| 6,004,279 A | 12/1999 | Crowley et al. |
| 6,019,736 A | 2/2000 | Avellanet et al. |
| 6,022,336 A | 2/2000 | Zadno-Azizi et al. |
| 6,022,363 A | 2/2000 | Walker et al. |
| 6,030,397 A | 2/2000 | Monetti et al. |
| 6,036,708 A | 3/2000 | Sciver |
| 6,056,721 A * | 5/2000 | Shulze .................... 604/101.05 |
| 6,066,158 A | 5/2000 | Engelson et al. |
| 6,080,170 A | 6/2000 | Nash et al. |
| RE36,764 E | 7/2000 | Zacca et al. |
| 6,090,118 A | 7/2000 | McGuckin, Jr. |
| 6,102,884 A | 8/2000 | Squitieri |
| 6,113,614 A | 9/2000 | Mears |
| 6,126,635 A | 10/2000 | Simpson et al. |
| 6,129,750 A | 10/2000 | Tockman et al. |

| | | | | | | |
|---|---|---|---|---|---|---|
| 6,143,009 | A | 11/2000 | Shiber | 6,402,745 B1 | 6/2002 | Wilk |
| 6,146,396 | A | 11/2000 | Konya et al. | 6,454,775 B1 | 9/2002 | Demarais et al. |
| 6,146,397 | A | 11/2000 | Harkrider, Jr. | 6,454,779 B1 | 9/2002 | Taylor |
| 6,152,909 | A | 11/2000 | Bagaoisan et al. | 6,482,215 B1 | 11/2002 | Shiber |
| 6,156,046 | A | 12/2000 | Passafaro et al. | 6,485,500 B1 | 11/2002 | Kokish et al. |
| 6,165,567 | A | 12/2000 | Ventzek et al. | 6,527,979 B2 | 3/2003 | Constanta et al. |
| 6,168,570 | B1 | 1/2001 | Ferrera | 6,602,264 B1 | 8/2003 | McGuckin, Jr. |
| 6,183,487 | B1 | 2/2001 | Barry et al. | 6,663,613 B1 | 12/2003 | Evans et al. |
| 6,185,449 | B1 | 2/2001 | Berg et al. | 2001/0031981 A1 | 10/2001 | Evans |
| 6,193,735 | B1 | 2/2001 | Stevens | | | |
| 6,203,561 | B1 | 3/2001 | Ramee et al. | | | |
| 6,206,898 | B1 | 3/2001 | Honeycutt et al. | | | |
| 6,217,595 | B1 | 4/2001 | Shturman et al. | | | |
| 6,221,042 | B1 * | 4/2001 | Adams ............... 604/96.01 | | | |
| 6,231,588 | B1 | 5/2001 | Zadno-Azizi | | | |
| 6,235,043 | B1 | 5/2001 | Reiley et al. | | | |
| 6,238,405 | B1 | 5/2001 | Findlay, III et al. | | | |
| 6,251,086 | B1 | 6/2001 | Cornelius et al. | | | |
| 6,254,550 | B1 | 7/2001 | McNamara et al. | | | |
| 6,264,667 | B1 | 7/2001 | McGuckin, Jr. | | | |
| 6,270,509 | B1 | 8/2001 | Barry et al. | | | |
| 6,287,271 | B1 | 9/2001 | Dubrul et al. | | | |
| 6,299,623 | B1 | 10/2001 | Wulfman | | | |
| 6,322,572 | B1 | 11/2001 | Lee | | | |
| 6,371,928 | B1 | 4/2002 | McFann et al. | | | |

FOREIGN PATENT DOCUMENTS

| | | |
|---|---|---|
| DE | 8900494 | 3/1989 |
| EP | 0177782 | 4/1986 |
| EP | 0452631 | 10/1991 |
| EP | 0709110 | 5/1996 |
| EP | 0815894 | 1/1998 |
| WO | 9923958 | 5/1999 |
| WO | 0154754 | 8/2001 |

OTHER PUBLICATIONS

Bacchus Vascular Solera Thrombectomy Catheter Brochure (Jan. 4, 2002).

* cited by examiner

DOUBLE BALLOON THROMBECTOMY CATHETER

CROSS REFERENCE TO RELATED APPLICATIONS

This application is a continuation of U.S. application Ser. No. 11/267,379 filed Nov. 4, 2005 now U.S. Pat. No. 7,645,261, which is a continuation of U.S. application Ser. No. 09/888,149 filed Jun. 22, 2001 now abandoned, which is a continuation-in-part of Patent Cooperation Treaty Application No. PCT/US00/41355 filed Oct. 20, 2000, which designates the United States, priority from the filing date of which is hereby claimed under 35 U.S.C. §120, which PCT application claims the benefit of U.S. Provisional Patent Applications No. 60/214,331 filed Jun. 27, 2000 and No. 60/161,124 filed Oct. 22,1999, the benefit of which is hereby claimed under 35 U.S.C. §119. The entire contents of each of these applications are hereby incorporated herein by reference.

BACKGROUND OF THE INVENTION

This invention relates to thrombectomy apparatus and procedures of the type generally disclosed in published Patent Cooperation Treaty Patent Application No. PCT/US98/15156.

SUMMARY OF THE INVENTION

In the course of a thrombectomy procedure, a clot is purged from the graft. Subsequently, the anastomoses are unplugged using two different types of balloons, preferably an angioplasty balloon for the venous side and a soft, compliant latex balloon for the arterial side. Both balloons are preferably positioned on a common catheter.

A catheter is used to deliver the wire for the dialysis thrombectomy procedure. The invention embraces the placement of the two balloons, namely, the preferably angioplasty balloon for the venous side, and preferably the soft, compliant balloon for the arterial side, on the delivery catheter.

In the course of practicing the method aspect of the invention and going forward with the thrombectomy procedure, the attending physician preferably proceeds to the venous side first, since blood endeavors to flow from the artery side to the vein side. Any blockage at the artery side means less blood flow through the graft, thereby facilitating opening of blockage or unplugging of the venous side. Typically, plaque to be cleared at the venous side is stronger and tougher than any plaque at the artery side. Accordingly, a tough angioplasty balloon, typically formed of a synthetic material, such as PET, is preferably used to unblock the venous side.

Plaque at the arterial side is generally not as hard, with a platelet plug often being encountered at the arterial side. The platelet plug is desirably pulled through the junction of the artery and the graft in order to unplug the arterial side.

In another aspect, this invention provides preferably disposable apparatus for performing mechanical thrombectomy cleansing of dialysis grafts where the apparatus preferably includes an axially-elongated catheter preferably having at least three axially-extending fluid communication passages therewithin, where a first one of the passages preferably has a rounded cross-section for free axial travel therealong of a guide wire inserted thereinto. In this aspect of the invention, the first balloon is desirably positioned along the exterior of the catheter proximate the first catheter end, with the interior of the first balloon being in fluid communication with a second one of the passageways. The first balloon, when inflated, is preferably generally spherical and positioned about the catheter so that the catheter defines an axis of the spherical balloon shape. The catheter desirably passes through the interior of the balloon when the first balloon is inflated.

In this aspect of the invention, a second balloon is desirably positioned along the exterior of the catheter inboard of the first balloon relative to the first catheter end, with the interior of the second balloon being in fluid communication with a third passageway. The second balloon when inflated desirably has an axially elongated generally cylindrical central portion and generally conical end portions, with the cylindrical and conical portions of the balloon being symmetrically positioned about the catheter. The catheter desirably passes through the interior of the second balloon when the second balloon is inflated. The catheter preferably further defines the axis of the cylindrical and conically-shaped portions of the balloon.

In this aspect of the invention, the catheter desirably further includes a pair of inflation ports which respectively communicate with the second and third passageways proximate the second end of the catheter. The passageways are preferably adapted for individual connectable communication with the source of pressurized gas for selectably inflating the first and second balloons by supply of pressurized gas thereto via the second and third passageways in the catheter.

The first balloon is desirably made of a compliant material, such as latex or polyurethane. The second balloon is desirably made of a substantially noncompliant material, such as PET or some other tough material.

The catheter exterior is desirably round, but may be other shapes or asymmetrical.

The invention further embraces the inclusion of radiopaque markers, preferably in the form of bands, on the catheter to facilitate imaging during the thrombectomy cleansing of dialysis grafts. The radiopaque markers are preferably positioned on the catheter to be within the interior of the respective balloons when the balloons are inflated.

In another aspect of the invention, an angioplasty balloon may be used for the arterial side of the graft and a soft "Fogarty style" latex balloon used for the venous side. Both balloons are preferably used on the same catheter. A clot is purged from a dialysis graft and then the anastomoses are unplugged by using the balloons, which are desirably of the two differing types.

DETAILED DESCRIPTION

Figure 1:
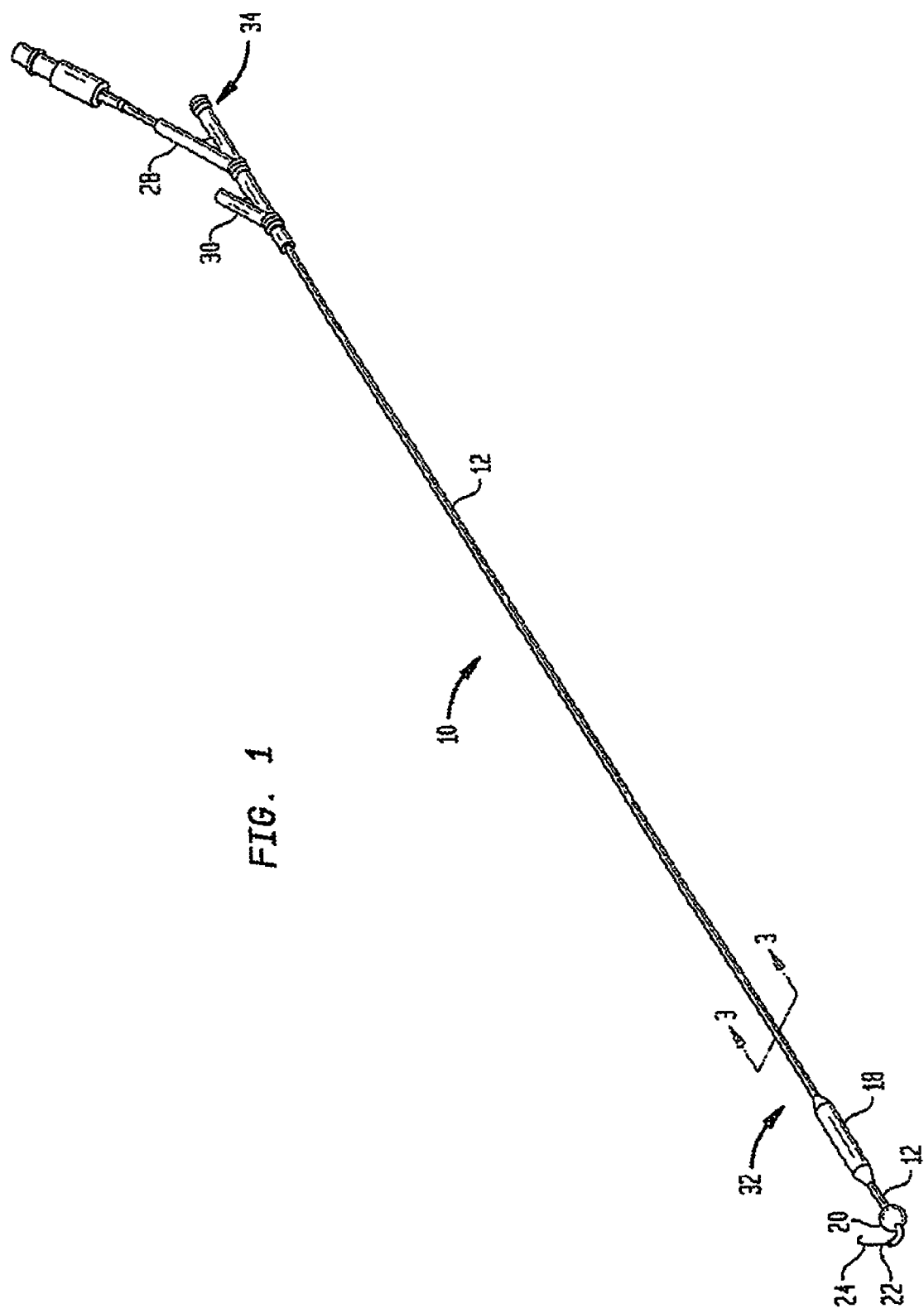
FIG. 1 is an isometric view in schematic form of a preferred double balloon thrombectomy catheter manifesting aspects of the invention.

When a dialysis graft is to be cleaned, blood flows through the dialysis graft from the arterial side to the vein side. Typically, the graft fills with clotting material as time passes and must be cleaned periodically in order for subsequent dialysis procedures to be completed successfully.

When dialysis grafts are cleaned, the loosened clotting material is desirably broken up at a location well upstream of that at which loosened particles of clotting material would flow downstream to the lungs. Accordingly, once the graft itself is cleaned, for example, using the approach and apparatus disclosed in the published PCT patent application referenced above, the juncture of the graft with the vein is desirably cleaned prior to cleaning the juncture of the graft with the artery. This is desirable because if the artery side was to be cleaned initially, this would increase the risk of loosened particles of clotting matter being released into the venous system.

When the venous anastomosis shows signs of narrowing, a physician or other attending health professional might opt to perform angioplasty on the venous side. Normally, an angioplasty balloon is used to unplug the juncture of the graft and the vein. Material gathering at the juncture of the graft and the vein tends to be plaque-like and is difficult to remove. Hence, a high-strength angioplasty balloon is preferably used for the graft-vein juncture cleaning procedure.

When the cleaning procedure is done at the juncture of the artery and the graft, in practicing the invention most often the physician or attending health care professional preferably uses a latex or other soft balloon. This is desirably accomplished by inserting a wire through the clotting material at the artery-graft juncture. The clotting material at the artery-graft juncture consists mostly of platelets. Once the wire is inserted from the graft through the platelets and into the artery, the latex balloon is inflated. The platelet plug is then pulled out of position at the juncture of the artery and the graft. This is accomplished by inflating the latex balloon positioned within the artery and then pulling the balloon against the platelet plug and into the graft; this is performed after the balloon has passed through the platelet plug in an uninflated condition. As a result, the platelet plug and clotting material are removed at the same time, sometimes permitting the clotting material and the platelet plug to be removed from the graft without an incision.

The conventional method of clearing the graft involves putting a thrombectomy device into the graft downstream of the arterial stenosis and breaking up the occluding matter. The device is then removed from the graft and reinserted upstream of the venous stenosis to ablate material in the direction of the arterial stenosis. Next the thrombectomy device is removed and a catheter with an angioplasty balloon on it is inserted into the graft to expand or unplug the venous stenosis. This catheter is then removed and a catheter with a compliant balloon is inserted into the graft to expand or unplug the arterial stenosis.

The number of times catheters must be removed and inserted into the graft increases the duration and/or complexity of the procedure and may weaken the graft due to the number of punctures that must be made in it.

The present invention simplifies the procedure used to clear dialysis grafts by placing balloons of different pressure ratings or strengths on the same catheter.

Referring to the drawings, a double balloon thrombectomy catheter according to one embodiment of the present invention is designated generally 10 and includes a catheter designated generally 12. Within catheter 12 are a major internal conduit designated generally 14 and secondary and tertiary internal conduits designated 16 and 26, respectively, for supply of liquid to the angioplasty or substantially noncompliant balloon and to a latex or substantially compliant balloon, respectively.

An angioplasty balloon designated generally 18 is mounted on the exterior of catheter 10. The interior of angioplasty balloon 18 communicates in a liquid-tight relationship with secondary internal conduit 16 within catheter 12 in order that angioplasty balloon 18 may be inflated by supply of pressurized liquid thereto via secondary internal conduit 16.

Double balloon thrombectomy catheter 10 further includes a balloon 20 made of a compliant material such as latex or polyurethane positioned as illustrated in the drawings on the exterior of catheter 12. Similarly to the balloon 18, the balloon 20 is positioned to communicate with the interior of tertiary internal conduit 26 in order that pressurized liquid may flow through tertiary internal conduit 26 and inflate the balloon 20. Alternatively, the balloon may be filled with a suitable gas, such as carbon dioxide.

A guide wire or rotatable thrombectomy wire 22 preferably having a J-shaped tip designated generally 24 is slidably resident within major internal conduit 14. Wire 22 may be advanced out of a distal end 32 of major internal conduit 14 within catheter 12 to perform thrombectomy procedures as described in published Patent Cooperation Treaty patent application PCT/US98/1 5156 identified above.

A connection port 28 is provided facilitating supply of pressurized liquid to secondary internal conduit 16. Similarly, another connection port 30 is supplied for furnishing pressurized liquid to tertiary internal conduit 26. Connection ports 28, 30 are preferably at the proximate end 34 of catheter 12, which is opposite distal end 32 of catheter 12 from which wire 22 emerges to perform the thrombectomy procedure.

Angioplasty balloon 18 is preferably configured with a cylindrical central portion, designated generally 36 and respective conical end portions each designated 38 as illustrated in the drawings.

While the invention has been described with reference to use of a latex or polyurethane balloon to remove the platelet plug anastomosis at the artery-graft juncture, the balloon may alternatively be made of other similar soft, compliant materials such as polyisoprene, which is a synthetic latex substitute and is well tolerated by persons who are latex intolerant.

Desirably, the angioplasty balloon is a PET or other semi- or noncompliant material capable of withstanding up to twenty (20) or more atmospheres of pressure. Hence, the angioplasty balloon can be inflated to a very high pressure and significant force may be generated when the balloon is inflated to press, against the plaque material and thereby open a passageway through the plaque material at the graft-vein juncture.

The angioplasty balloon 18 desirably has a "rewrap" characteristic, so that the balloon rewraps tightly about itself when deflated, to ease insertion and removal of the balloon through introductory sheaths.

Optionally and desirably, radiopaque markers, most desirably in the form of marker bands 21, 31, may be provided, preferably on the exterior of catheter 10. These radiopaque markers are desirably provided positioned on catheter 10 so that the marker bands 21, 31 are within the interior of the balloons 18 and 20, respectively, when those balloons are inflated in the manner illustrated in FIG. 2. However, positioning of the radiopaque markers is not limited to that illustrated in FIG. 2; the radiopaque markers need not be within one or both of the balloons when the balloons are inflated. So long as the attending physician knows the location of the radiopaque markers vis-à-vis that of the balloons, the angioplasty procedure may go forward with the balloon-carrying catheter being guided radiographically.

Figure 3:
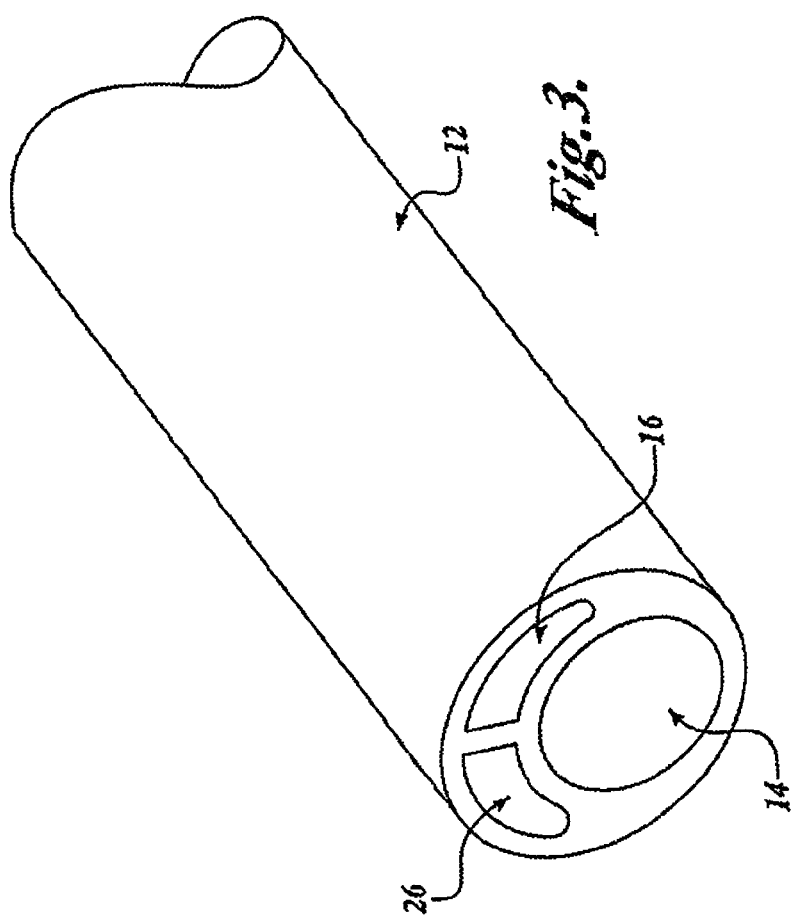
FIG. 3 is a sectional view of the tubular portion of the double balloon thrombectomy catheter illustrated in FIGS. 1 and 2 taken at lines and arrows 3-3 in FIG. 1.
Figure 4:
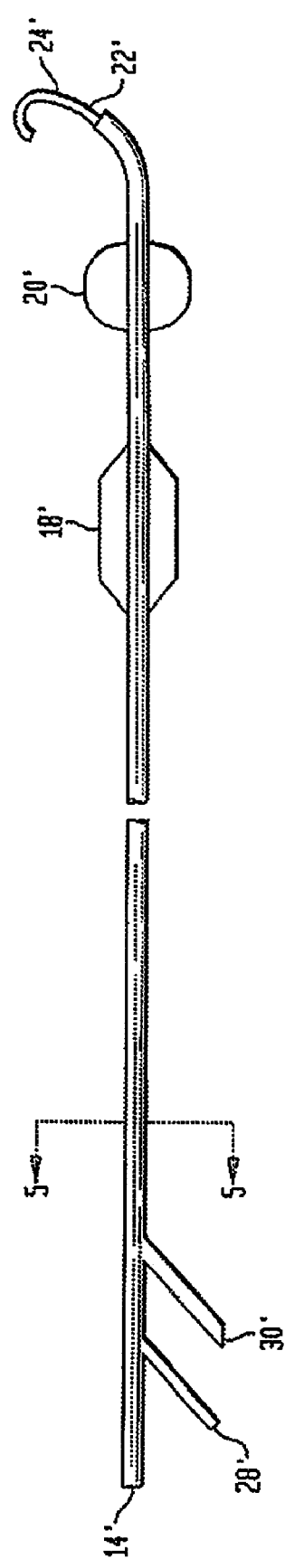
FIG. 4 is a schematic side view of another form of a double balloon thrombectomy catheter manifesting aspects of the invention.
Figure 5:
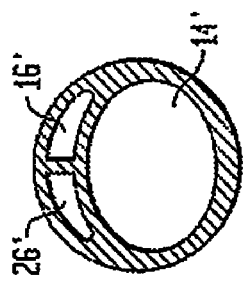
FIG. 5 is a sectional view of the double balloon thrombectomy catheter illustrated in FIG. 4 taken at lines and arrows 5-5 in FIG. 4.

In the alternate embodiment of FIGS. 4 and 5, the catheter has an internal conduit 14' and connection ports 28', 30' for inflating balloons 18' and 20'. Internal conduit 14' is oval shaped; internal conduits 26' and 16' are shaped similarly to conduits 26 and 16 of FIG. 3. Thrombectomy wire 22' has a J-shaped tip 24'.

Figure 2:
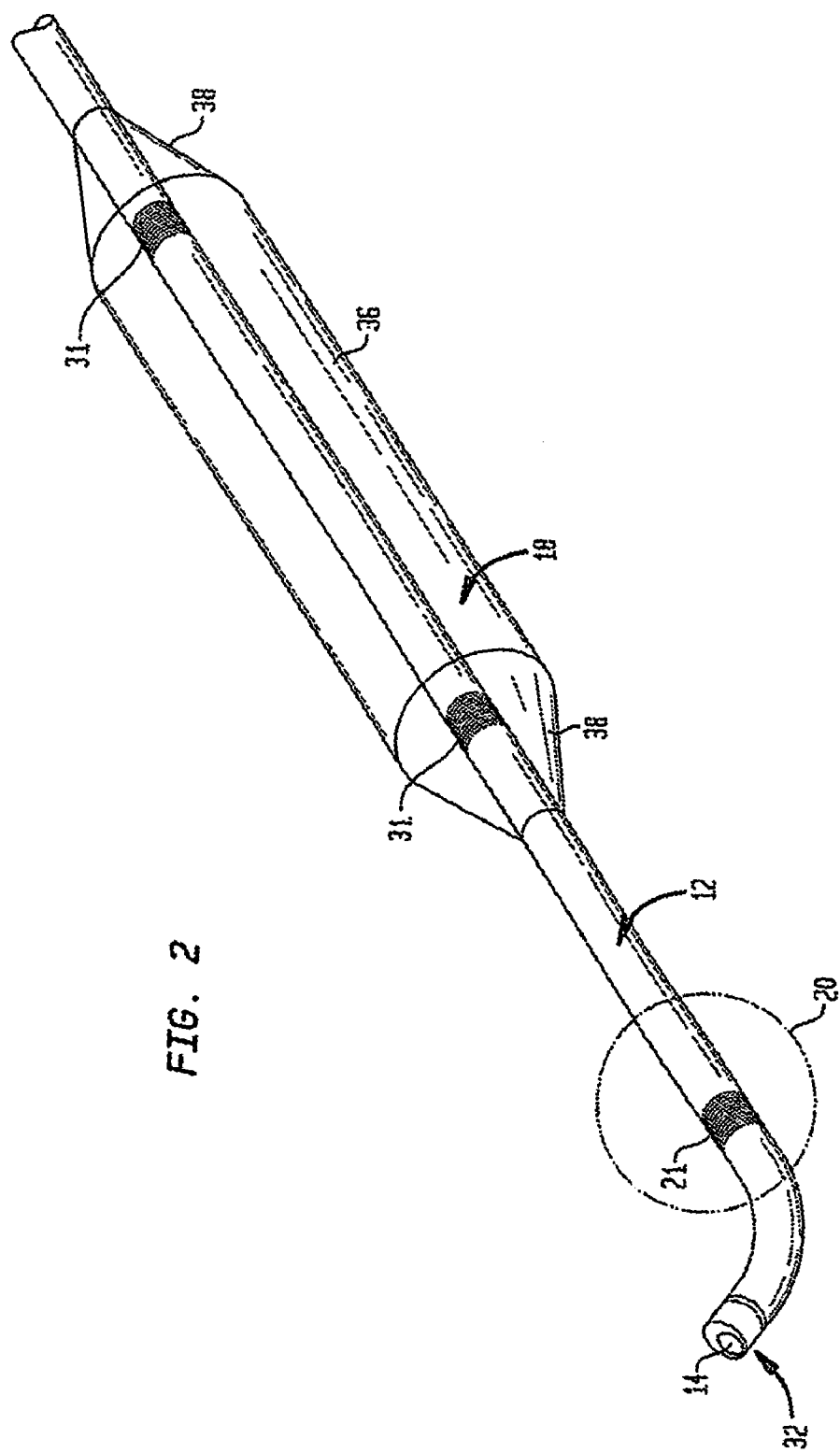
FIG. 2 is an enlarged schematic isometric view of the preferred double balloon thrombectomy catheter illustrated in FIG. 1 showing the two balloons in larger form with radiopaque markers in place on the catheter to facilitate imaging.

While the invention has been described as preferably embracing an angioplasty balloon and a softer latex balloon preferably mounted on a common catheter, the position of the balloons may be reversed from that illustrated in FIG. 2, the balloons may be differently configured from what is illustrated in FIG. 2, two balloons of the same type may be used on the catheter, and the like. Similarly, although the balloon 18 is referred to as an angioplasty balloon, other balloon styles that are capable of withstanding the pressure required to expand a venous side stenosis could be used. Similarly, the compliant balloon 20 can be any balloon that is strong enough to clear an arterial side blockage.

With the present invention, a physician can use a single catheter to perform a dialysis graft thrombectomy procedure.

A catheter having at least two balloons as described above is inserted into the graft preferably at a point where the catheter can be redirected toward the venous stenosis or the arterial stenosis without removing the catheter from the graft. In one embodiment of the invention, the catheter is inserted into the approximate midpoint of a "U-shaped" dialysis graft. The clotting material in the graft is then removed in the direction of the stenosis at each end of the graft (in either order) using a thrombectomy device placed in the large lumen of the catheter, run over the guide wire, or by using the guide wire itself, such as by rotating the guide wire.

Next, the high pressure balloon is used to expand the stenosis at the venous junction. Finally, the low pressure compliant balloon is used to pull the platelet plug from the arterial junction.

Finally, the dual catheter is not limited to only clearing dialysis grafts. The catheter could be used in any procedure where balloons of different compliancies were previously used on different catheters.

While the present invention has been described with respect to its currently preferred embodiment, it will be appreciated that changes could be made without departing from the scope of the invention. Therefore, the scope of the invention is to be determined solely from the following claims and equivalents thereof.

The invention claimed is:

1. A method for performing mechanical thrombectomy comprising the steps of:
   providing a catheter having a distal portion, a proximal portion, an internal passageway, a first axially elongated conduit and a first balloon, the catheter inserted into a patient's body with the first balloon in the deflated condition;
   exposing a rotatable wire from the internal passageway of the catheter to expose a non-linear distal tip portion so that the distal tip portion extends distal of the first balloon and distal of a distalmost end of the catheter; and
   rotating the wire to perform a mechanical thrombectomy procedure to break up thrombus in an area distal of the first balloon and distal of the distalmost end of the catheter.

2. The method of claim 1, further comprising the step of injecting fluid through the first conduit to inflate the first balloon.

3. The method of claim 2, wherein the step of injecting fluid through the first conduit is performed subsequent to the step of rotating the wire.

4. The method of claim 3, wherein the step of inflating the first balloon expands a stenosis.

5. The method of claim 3, wherein the first balloon is an angioplasty balloon, and the step of inflating the first balloon causes the first balloon to form a shape having conical end portions.

6. The method of claim 2, wherein the catheter includes a second balloon and a second axially elongated conduit, and the method includes the step of injecting fluid through the second conduit to inflate the second balloon from a deflated condition.

7. The method of claim 6, wherein the step of rotating the wire to perform the thrombectomy procedure is performed with the first and second balloons in the deflated condition.

8. The method of claim 6, wherein the method includes sliding the wire relative to the internal passageway to expose the wire from the catheter to perform the thrombectomy procedure.

9. The method of claim 8, wherein the rotatable wire further functions as a guide wire for the body.

10. The method of claim 6, further comprising the step of utilizing the second balloon to pull an arterial plug.

11. The method of claim 6, wherein the first balloon is an angioplasty balloon having a first compliancy, and the second balloon has a second compliancy less than the first compliancy, the first balloon being positioned between the second balloon and a proximal portion of the catheter.

12. The method of claim 6, wherein the first and second balloons have different pressure ratings.

13. The method of claim 1, wherein the method includes sliding the wire relative to the internal passageway to expose the wire from the catheter to perform the thrombectomy procedure.

14. The method of claim 1, wherein the step of rotating the wire to perform the mechanical thrombectomy procedure is performed with the first balloon in the deflated condition.

15. The method of claim 1, wherein the catheter includes a radiopaque marker and the method includes visualizing the radiopaque marker to guide the catheter.

16. The method of claim 1, wherein the first balloon includes a radiopaque marker and the method includes the step of radiographically guiding the catheter.

17. The method of claim 1, wherein the rotatable wire further functions as a guide wire for the catheter.

* * * * *